(12) United States Patent
Potapov et al.

(10) Patent No.: US 8,442,357 B2
(45) Date of Patent: May 14, 2013

(54) METHOD FOR RECONSTRUCTING TWO-DIMENSIONAL CHEMICAL MAPS FROM ELECTRON SPECTROSCOPY LINE SCANS

(75) Inventors: Pavel Potapov, Dresden (DE); Hans-Jürgen Engelmann, Dresden (DE)

(73) Assignee: Globalfoundries Inc., Grand Cayman (KY)

( * ) Notice: Subject to any disclaimer, the term of this patent is extended or adjusted under 35 U.S.C. 154(b) by 272 days.

(21) Appl. No.: 13/051,431

(22) Filed: Mar. 18, 2011

(65) Prior Publication Data
US 2012/0237138 A1    Sep. 20, 2012

(51) Int. Cl.
*G06K 9/32* (2006.01)

(52) U.S. Cl.
USPC ........... 382/294; 136/265; 250/307; 250/311; 257/749; 428/141; 700/182

(58) Field of Classification Search ........................ None
See application file for complete search history.

(56) References Cited

U.S. PATENT DOCUMENTS

| | | | |
|---|---|---|---|
| 7,154,091 B2 * | 12/2006 | Zewail et al. | 250/311 |
| 7,317,964 B1 * | 1/2008 | Spowart et al. | 700/182 |
| 7,880,142 B2 * | 2/2011 | Skoglund | 250/307 |
| 8,247,769 B2 * | 8/2012 | Zewail | 250/311 |
| 2008/0026181 A1 * | 1/2008 | Rastogi et al. | 428/141 |
| 2010/0108882 A1 * | 5/2010 | Zewail | 250/307 |
| 2010/0108883 A1 * | 5/2010 | Zewail | 250/307 |
| 2010/0180950 A1 * | 7/2010 | Gao et al. | 136/265 |
| 2010/0230814 A1 * | 9/2010 | Marks et al. | 257/749 |
| 2010/0270497 A1 * | 10/2010 | Hezeque et al. | 252/182.1 |

OTHER PUBLICATIONS

English translation of Office Action for related German Patent Application No. 10 2011 084 450.3 dated Nov. 15, 2011, pp. 1-2.
Heidelmann, M et al., "StripeSTEM, a technique for the isochronous acquisition of high angle annular dark-field images and monolayer resolved electron energy loss spectra", Ultramicroscopy 109 (2009) 1447-1452.

* cited by examiner

*Primary Examiner* — Tsung-Yin Tsai
(74) *Attorney, Agent, or Firm* — Ditthavong Mori & Steiner, P.C.

(57) ABSTRACT

Two-dimensional chemical maps of a layered nanostructure are reconstructed from selected spectroscopy line scans in a scanning electron microscope. Embodiments include fast two-dimensional scanning a layered nanostructure to form a structure image having multiple layers, slow-rate spectroscopy scanning the nanostructure along selected scanning lines to form chemical profiles, warping the structure image into a warped structure image by flattening each of the layers in the structure image, aligning chemical profiles to the warped structure image, forming warped chemical maps, and inversely transforming the warped chemical maps into two-dimensional chemical maps.

20 Claims, 5 Drawing Sheets

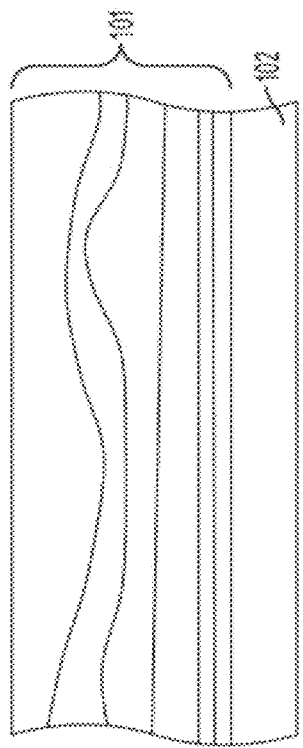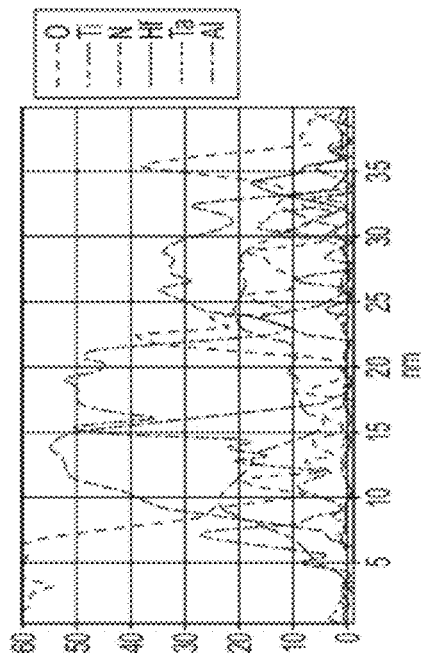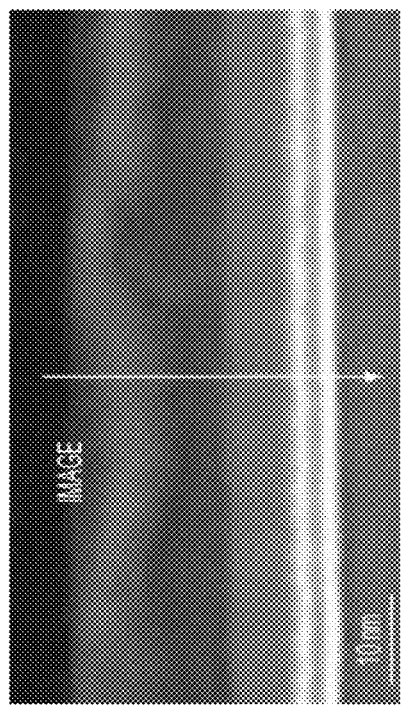

US 8,442,357 B2

METHOD FOR RECONSTRUCTING TWO-DIMENSIONAL CHEMICAL MAPS FROM ELECTRON SPECTROSCOPY LINE SCANS

TECHNICAL FIELD

The present disclosure relates to reconstructing two-dimensional chemical maps from spectroscopy line scans by using a scanning electron microscope. The present disclosure is particularly applicable to two-dimensional chemical maps of semiconductor structures in 32 nanometer technologies and beyond.

BACKGROUND

To develop and optimize a layered nanostructure, for example, a biologic specimen, an environmental sample, a semiconductor structure, etc., a scanning electron microscope with a resolution of 1 nm and below is commonly used to scan the nanostructure to obtain a characterization of, for example, chemical elements of the target compositions, pollutants, or defects. By way of example, the nanostructure may be a semiconductor replacement gate structure, as depicted in FIG. 1A, that includes different layers 101 such as a high k dielectric, a work function layer, barriers and metal gate electrodes deposited on a silicon (Si) substrate 102. The nanostructure can be examined in the scanning transmission electron microscope (STEM) by fast two-dimensional scanning of the electron probe and registering the signal from an annular dark-field (ADF) or bright-field (BF) detector. Such fast ADF/BF scanning provides an image of the nanostructure revealing the general morphology of the layers as seen in FIG. 1B. However, it fails to provide specific chemical information, i.e., chemical maps.

Slow-rate STEM scanning in conjunction with an energy-dispersive X-ray spectroscopy (EDS) or electron energy loss spectroscopy (EELS) can examine the distribution of chemicals in the nanostructure as depicted in FIG. 1C. For example, with the transmission illumination scheme of the STEM, the electron probe passing through a sufficiently thin specimen generates the characteristic X-ray radiation, which can be captured by the EDS detector and used for chemical analysis. The EDS signal can be obtained simultaneously with the ADF/BF signal, allowing direct correlation of image and chemical data. However, EDS or EELS spectroscopy requires much longer acquisition from each position of the electron probe as compared with simple ADF/BF STEM scanning. Thus, the spectra are usually taken by scanning not over the entire surface of the nanostructure but rather along one line or a few lines, with further extraction of the chemical profiles along a few directions, as depicted in FIG. 1C. Such chemical profiles are typically noisy and fail to reveal the two-dimensional distribution of chemicals in the nanostructure. Attempts to produce two-dimensional chemical maps have been confronted with the above-mentioned intrinsic slow rate of spectroscopy scanning. For example, the spectroscopic scanning of a frame of 100×100 pixels may take a few hours per frame (as opposed to one second per frame by fast ADF/BF scanning) to achieve a desirable signal-to-noise ratio (e.g., 5 to 10).

To accelerate two-dimensional chemical mapping, dedicated instruments for fast spectroscopy have been introduced. However, they apply a very high electron current (e.g., 0.5 to 1.5 nanoamps (nA)) into the small investigated area, which may incur in-situ damage to the sample and degrade the resolution of the imaging. As a result, the signal-to-noise ratio is often compromised with the resolution in such chemical maps. In addition, the dedicated fast spectrometers are expensive.

A need therefore exists for methodology to accelerate two-dimensional chemical imaging of nanostructures using existing STEM spectrometers with a low electron current while maintaining a desirable signal-to-noise ratio and resolution.

SUMMARY

An aspect of the present disclosure is a method of reconstructing two-dimensional chemical maps from an image formed by fast ADF/BF scanning the nanostructure and slow-rate scanning along selected scanning lines with collecting spectra.

Additional aspects and other features of the present disclosure will be set forth in the description which follows and in part will be apparent upon examination of the following or may be learned from the practice of the present disclosure. The advantages of the present disclosure may be realized and obtained as particularly pointed out in the appended claims.

According to the present disclosure, some technical effects may be achieved in part by a method including: fast two-dimensional BF/ADF scanning a layered nanostructure with an electron microscope to form a structure image having multiple layers; slow-rate scanning the nanostructure along selected scanning lines with collecting characteristic spectra; extracting chemical profiles of the nanostructure from the spectra, transforming the structure image into a warped structure image by flattening each of the layers in the structure image; aligning the coordinates of the chemical profiles with those of the warped structure image, averaging the chemical profiles obtained from different scan lines, expanding the averaged profiles into warped chemical maps; and inversely transforming the warped chemical maps respectively into two-dimensional chemical maps.

Aspects of the method include slow-rate scanning the nanostructure along a few selected scanning lines. Another aspect includes extracting a chemical profile including one or more chemical elements based on the obtained spectra. Additional aspects include transforming the structure image into a warped structure image by defining the morphology of the layers in the structure image by a criterion of equal signal levels, wherein the warped structure image shows no structural change along an axis within the plane of each of the layers. Further aspects include transforming the structure image into the warped structure image using a transformation formula; and inversely transforming the warped chemical maps into the two-dimensional chemical maps using a reverse transformation formula corresponding to the transformation formula. Other aspects include the transformation formula being a warping matrix that continuously transforms the structure image while preserving a topology of the structure image, for example by warping in one or two spatial directions. Additional aspects include transforming the chemical profiles into one averaged chemical profile by: aligning the chemical profiles to the coordinates of the warped image; and summing and averaging the chemical profiles, such as by using the warping matrix. Another aspect includes expanding the averaged chemical profiles, and forming warped chemical maps having no chemical change along one axis of the layers. Further aspects include slow-rate scanning the nanostructure along selected scanning lines with employing electron energy loss spectroscopy, energy-dispersive X-ray spectroscopy, cathode luminescence spectroscopy, or other spectroscopy employed in electron microscopy. Other aspects include minimizing the electron dose required for the comprehensive chemical characterization of the nanostructure.

Another aspect of the present disclosure is a method including fast two-dimensional scanning a layered nanostructure with an electron probe with registering an ADF or BF detector signal to provide an image of the nanostructure, the image having multiple layers; generating a warped image by aligning the layers in the image using a warping matrix; collecting spectra of the nanostructure along selected scan lines; extracting chemical profiles from the collected spectra; aligning and averaging the chemical profiles; generating warped chemical maps from the averaged chemical profiles, the warped chemical maps having no chemical change along one axis of the layers; and applying an inverse of the warping matrix to the warped chemical maps to form two-dimensional chemical maps of the nanostructure.

Aspects of the method include extracting chemical profiles from the spectra collected when scanning along a few selected lines. Further aspects include each chemical profile including multiple chemical elements. Other aspects include generating warped chemical maps by: aligning and averaging chemical profiles for each chemical element; and expanding the averaged chemical profiles to generate warped chemical maps having no chemical change along one axis within the plane of each layer. Other aspects include the warping matrix continuously transforming the image of the nanostructure while preserving a topology of the image. Further aspects include the warping matrix transforming the structural image by warping in one or two spatial directions. Additional aspects include extracting chemical profiles, or profiles of any other material characteristic value, from the electron probe scanned along the predetermined lines while employing electron energy loss spectroscopy, energy-dispersive X-ray spectroscopy, cathode luminescence spectroscopy, or other spectroscopy applicable to an electron microscopy.

Another aspect of the present disclosure is a method including fast two-dimensional scanning a layered semiconductor nanostructure with an electron probe to form an image having multiple layers; slow-rate scanning the nanostructure along a predetermined number of scan lines to form chemical profiles, each chemical profile corresponding to one of the scan lines and including one or more chemical elements; transforming the image into a warped image by: defining a morphology of the layers in the image with a criteria of equal signal levels, and forming a warped image using a warping matrix that continuously transforms the image while preserving a topology of the image, wherein the warped image shows no structural change along each of the layers; aligning coordinates of the chemical profiles with those of the warped image; averaging chemical profiles from different line scans for each chemical element; expanding an averaged chemical profile into warped chemical maps, wherein each of the warped chemical maps exhibits no chemical change along an axis within the plane of each layer; and inversely transforming the warped chemical maps into two-dimensional chemical maps using a reverse warping matrix corresponding to the warping matrix. Aspects of the method include fast two-dimensional scanning the semiconductor nanostructure with registering the signal from an ADF or BF detector to form an image of the nanostructure.

Additional aspects and technical effects of the present disclosure will become readily apparent from the following detailed description wherein embodiments of the present disclosure are described simply by way of illustration of the best mode contemplated to carry out the present disclosure. As will be realized, the present disclosure is capable of other and different embodiments, and its several details are capable of modifications in various obvious respects, all without departing from the present disclosure. Accordingly, the drawings and description are to be regarded as illustrative in nature, and not as restrictive.

BRIEF DESCRIPTION OF THE DRAWINGS

The present disclosure is illustrated by way of example, and not by way of limitation, in the figures of the accompanying drawing and in which like reference numerals refer to similar elements and in which:

FIG. 1A schematically illustrates a conventional semiconductor structure; FIG. 1B illustrates a nanostructure image obtained with a fast two-dimensional scan of the structure with capturing the ADF signal; and FIG. 1C illustrates the chemical profile along the line indicated in FIG. 1B obtained with conventional electron microscopy techniques;

DETAILED DESCRIPTION

In the following description, for the purposes of explanation, numerous specific details are set forth in order to provide a thorough understanding of exemplary embodiments. It should be apparent, however, that exemplary embodiments may be practiced without these specific details or with an equivalent arrangement. In other instances, well-known structures and devices are shown in block diagram form in order to avoid unnecessarily obscuring exemplary embodiments. In addition, unless otherwise indicated, all numbers expressing quantities, ratios, and numerical properties of ingredients, reaction conditions, and so forth used in the specification and claims are to be understood as being modified in all instances by the term "about."

The present disclosure addresses and solves the problem of slow scanning processing attendant upon generating two-dimensional chemical maps of a nanostructure using scanning electron microscopes. In accordance with embodiments of the present disclosure, the characteristic spectra required for chemical analysis are taken when scanning along only a few selected lines instead of scanning over the whole surface of the nanostructure. Thereafter, two-dimensional chemical maps can be reconstructed from the spectroscopic information obtained along these lines and a structure image obtained by fast two-dimensional scanning over the whole surface of the nanostructure, without collecting the spectra.

Methodology in accordance with embodiments of the present disclosure includes obtaining a structure image by fast two-dimensional scanning with collecting the signal from annular dark-field (ADF) detector, slow scanning along a few line scans with collecting the characteristic spectra, extracting the signal for each chemical element from the spectra collected along each line scan, forming the chemical profiles corresponding to each line scan where each chemical profile may include profiles of one or more elements, finding the warping matrix which transforms the original structure image into a warped structure image by flattening all visible layers, aligning each chemical profile with the warped image, averaging chemical profiles resulting in a low-noise averaged chemical profile, expanding the averaged chemical profile into two-dimensional warped maps, and inverse transforming of the warped chemical maps into unwarped two-dimensional chemical maps.

Still other aspects, features, and technical effects will be readily apparent from the following detailed description, wherein preferred embodiments are shown and described, simply by way of illustration of the best mode contemplated. The disclosure is capable of other and different embodiments, and its several details are capable of modifications in various obvious respects. Accordingly, the drawings and description are to be regarded as illustrative in nature, and not as restrictive.

Figure 2C:
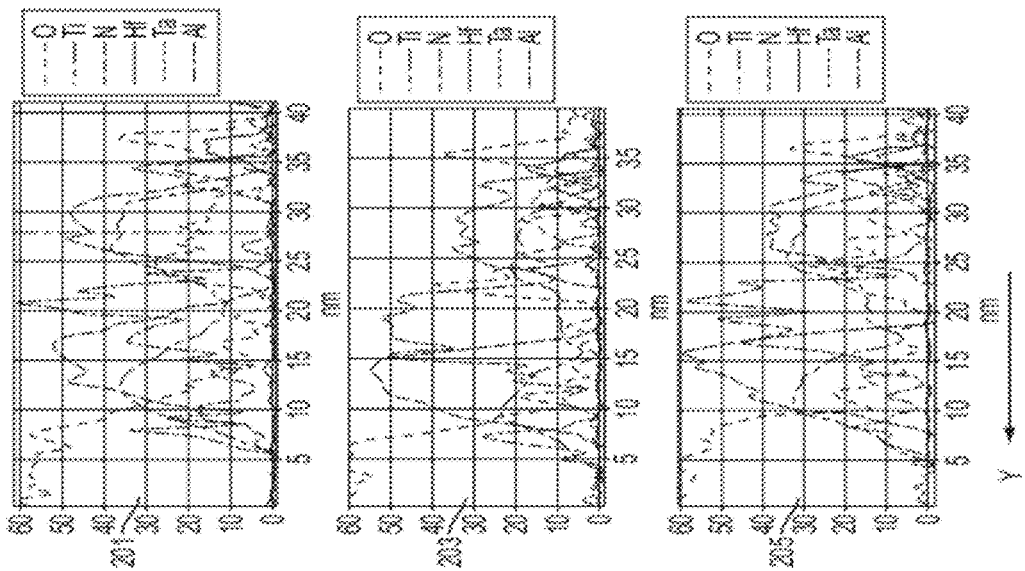
FIG. 2C illustrates the extracted chemical profiles along the line scans indicated in FIG. 2A.
Figure 2A:
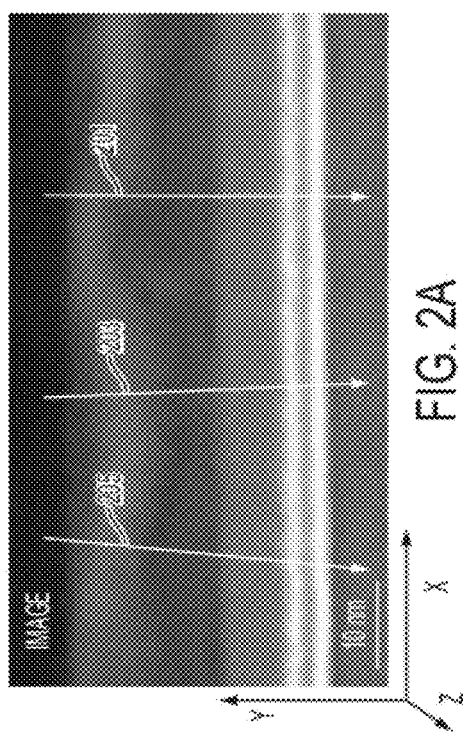
FIG. 2A illustrates a nanostructure image obtained with a fast two-dimensional scan of the structure with capturing the ADF signal, in accordance with an exemplary embodiment.
Figure 2B:
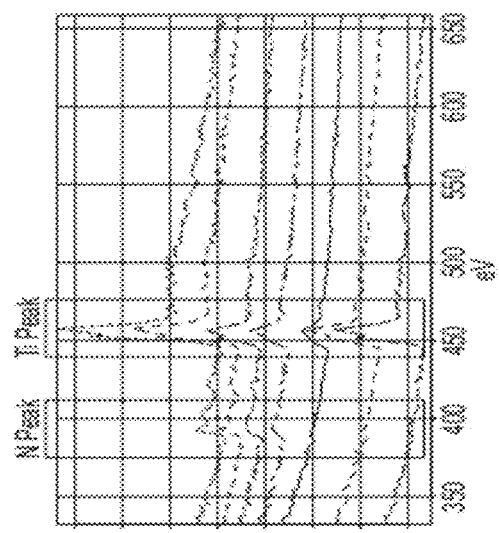
FIG. 2B illustrates the typical EELS spectra obtained when spectroscopy line scans are performed, in accordance with an exemplary embodiment.
Figure 2F:
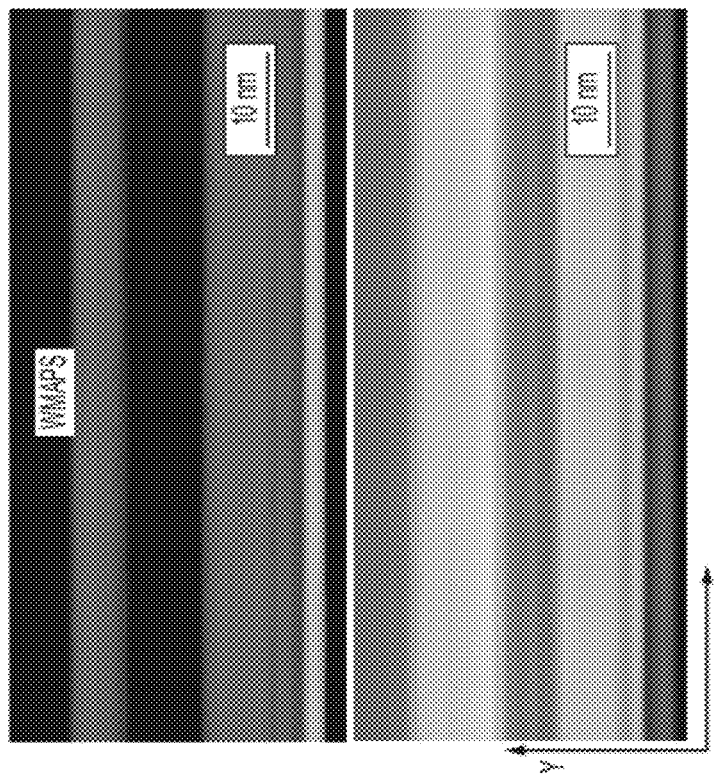
FIG. 2F illustrates Wmaps obtained, in accordance with an exemplary embodiment.

FIGS. 2A through 2G show examples of images obtained the various steps of a process, in accordance with an exemplary embodiment. FIG. 3 is a flowchart illustrating the process flow, in accordance with an exemplary embodiment. FIG. 2A shows the definition of the spatial coordinates used through the present disclosure. In the employed scheme of scanning transmission electron microscopy (STEM), the electron beam is directed along the Z direction and penetrates the sample within a small spot having a diameter typically a few fractions of a nanometer. The sample thickness is typically several tens of nanometers in the Z direction, thus the obtained information is integrated over a few tens of nanometers on the way of the electron beam through the sample. However, as the samples in STEM are usually prepared from structures which show significant variation of morphology/chemistry in the XY direction with an insignificant one in the Z direction, the penetration spot (hereinafter "probe") may be then scanned along the X-Y direction. In step 301, the electron probe is fast scanned over the whole surface of the nanostructure while the ADF detector signal is collected. Using this signal, an image of the nanostructure (hereinafter "Image") is formed in step 303, as shown in FIG. 2A.

In addition, in step 305, slow scanning along a few selected lines with collecting EDS and EELS spectra is performed. FIG. 2B shows in an overlapping manner the examples of the collected EELS spectra (energy in eV along the horizontal axis, count number along the vertical axis) with the characteristic peaks indicating the content of Ti and N within the probe. The figure serves a purely illustrative purpose as spectra are collected at a much larger number of probe positions along a line scan and within a much wider energy range. Simultaneously EDS spectra (not shown) are collected from each probe position. For collecting spectroscopy information (e.g., EDS, EELS), the probe needs to stay at a specific point of the nanostructure for a sufficiently longer time than is necessary for simple imaging with an ADF detector. In accordance with an exemplary embodiment, a limited number of lines are scanned across the specimen instead of the scanning the entire surface of the nanostructure, and, therefore, the chemistry of the nanostructure can be characterized over a much shorter time period.

Line scans should go in the direction approximately perpendicular to the visible layers in the Image (for example, the layers in FIG. 2A spread generally along the X axis while the line scans depicted by arrows 201, 203, and 205 move generally along the Y axis and are only slightly angled from the Y axis. The directions of the selected scanning lines should not necessarily be precisely parallel but rather should be approximately aligned with one another.

Although three line scans are shown in FIG. 2A, the number is merely illustrative. The number of scanning lines may be determined based on a desirable resolution/granularity of the two-dimensional chemical maps, a desirable precision/accuracy of the final two-dimensional chemical maps, a desirable signal-to-noise ratio of the two-dimensional chemical maps, etc. Taking a single linescan would generate undesirable noisy chemical profiles. Although the selected number depends on the above-mentioned factors, typically at least five line scans should be performed for an appropriate signal to noise ratio.

In step 307, a multiple chemical profile consisting of profiles of one or more elements along each line scan is extracted from the EELS and EDS spectra. FIG. 2C shows the chemical profiles obtained along the line scans 201, 203, and 205. The standard extraction techniques known from the theory of EELS and EDS spectroscopy are used. Each chemical profile has as the horizontal axis a distance along the Y axis, as defined in FIG. 2A, from a scanning starting point and measured in nm (e.g., 0 to 45 nm), and as the vertical axis a content in atomic %. In the shown example, oxygen (O), nitrogen (N), and titanium (Ti) chemical profiles were extracted from EELS spectra and hafnium (Hf), tantalum (Ta), aluminum (Al) profiles were extracted from the EDS spectra. Depending on the chemical composition of the investigated nanostructure, the signals from other elements retrievable by EELS and EDS can be extracted and further processed. In the shown example, EDS and EELS are employed as the most common spectroscopy techniques in the electron microscopy. Nevertheless, other spectroscopy techniques applicable to electron microscopy, for instance cathode luminescence, may alternatively be employed. Furthermore, depending on the employed spectroscopy technique, the methodology allows processing not only the chemical composition but also bonding variation, strain and any other material characteristic value extractable from the employed spectroscopy technique.

In accordance with an exemplary embodiment, it is assumed that the majority of the nanostructure includes a sequence of layers, whose geometry can be readily deduced from the Image of FIG. 2A. It is further assumed that the chemical composition does not change significantly across each layer (e.g., in nearly the X direction or Z direction) but may vary dramatically in the direction perpendicular to the layers (e.g., along the Y axis). Given these assumptions, the distribution of chemicals should unambiguously correlate with the morphology of the layers visible in the Image. Furthermore, the morphology of the layers can be retrieved from the Image based on the criteria of equal ADF signal levels. These assumptions are employed in step 309, in which a transformation formula, namely a warping matrix, is determined for warping the original Image of FIG. 2A into an image shown in FIG. 2D. In the warped image (hereinafter "Wimage") the layers are aligned along the Y axis and appear to be flat in the X direction. In other words, the Wimage shows no or little variation of the ADF signal in the X direction while showing significant variation along the Y direction.

Figure 2D:
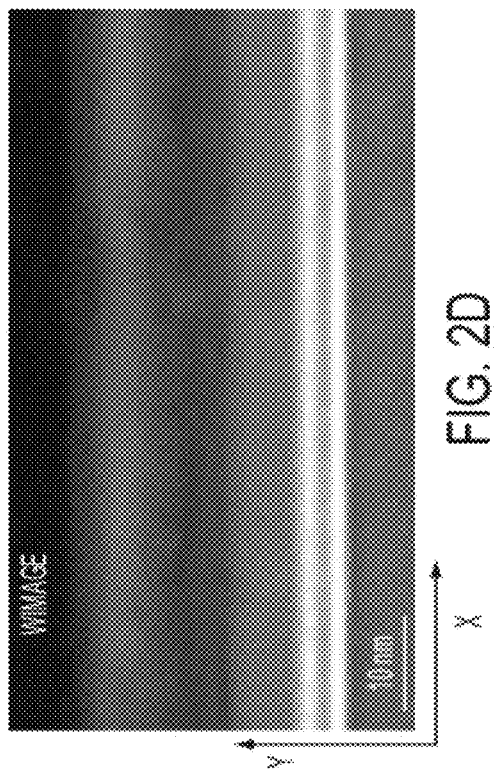
FIG. 2D illustrates a Wimage obtained, in accordance with an exemplary embodiment.
Figure 3:
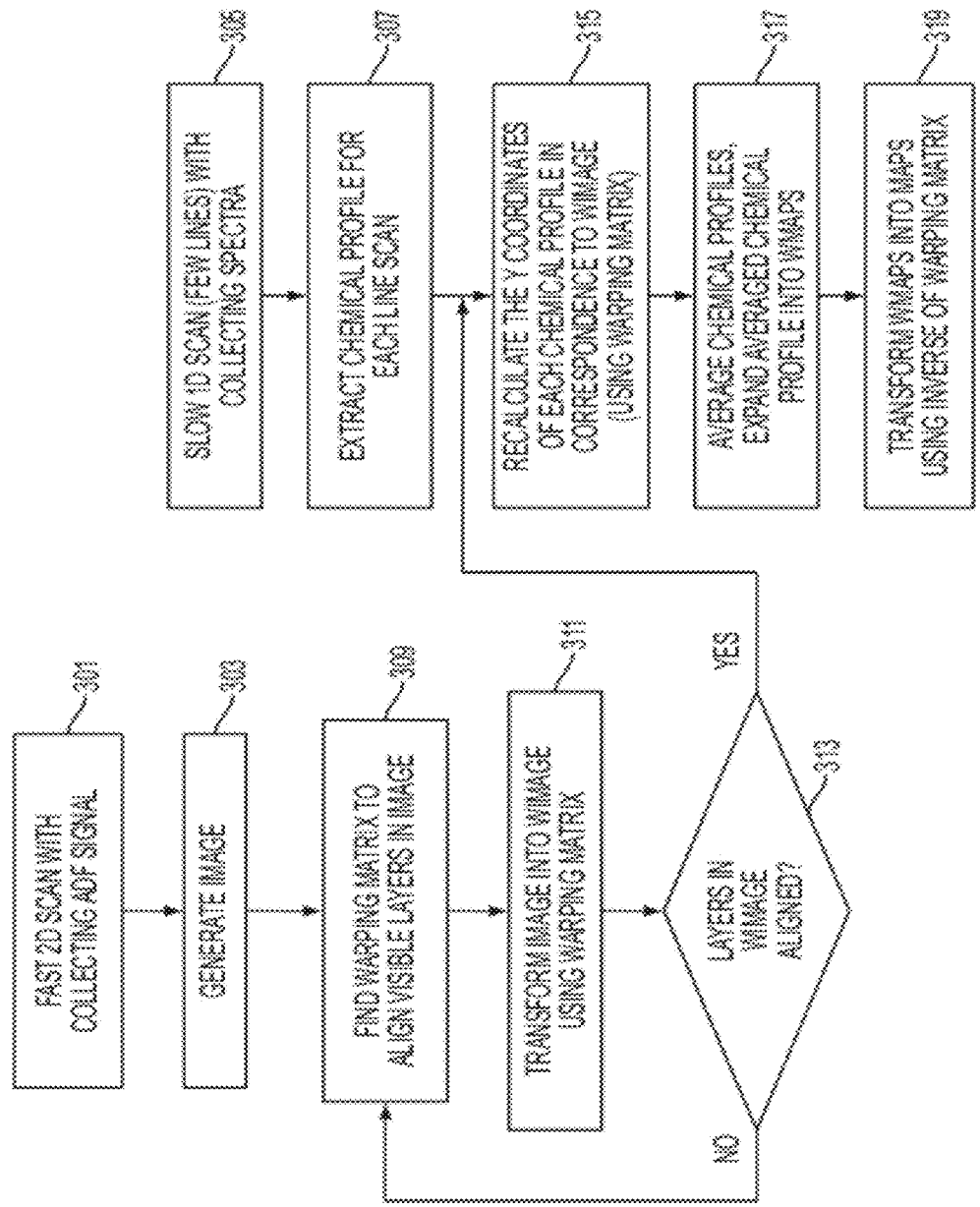
FIG. 3 is a flowchart illustrating a process flow for construction of two-dimensional chemical maps, in accordance with an exemplary embodiment.

The warping matrix crucial for the present methodology is a matrix transforming an original digital image to a final image with all visible layers aligned one to another in the Y direction while appearing as flat as possible in the X direction (FIG. 2D). Technically, the Warping Matrix assigns each pixel (Xf,Yf) of the final image to the value taken from the pixel (Xo,Yo) of the original image in such a manner that the final image satisfies the above mentioned criteria. Therefore, the Warping Matrix consists of twice as many pixels as in the final image, as for each given pixel (Xf,Yf) the Warping Matrix should point the coordinates Xo and Yo of the original pixel. If the layers are not bent strongly, warping only in the Y-direction might be sufficient. In that case, the equality Xf=Xo may be assumed and the only correspondence between Yf and Yo needs to be defined, therefore the size of the Warping Matrix is equal to that of the final image. The Warping matrix may be calculated based upon the morphology of layers in the original Image by using any appropriate warping algorithms known from digital image processing theory. The applied warping transformation should satisfy the following conditions: (1) be continuous and (2) preserve the topology of the original image.

In step 311, the warped Wimage is generated using the calculated warping matrix. The Wimage is used to control the quality of the warping matrix, as a more accurately calculated warping matrix yields better visually aligned layers in the Wimage. If the layers in the Wimage appear insufficiently aligned and not perfectly flat as determined in step 313, steps 309 and 311 should be repeated, with the warping matrix being recalculated and the Wimage being regenerated. If the layers in the Wimage appear sufficiently aligned and perfectly flat as determined in step 313, the process proceeds to step 315.

In step 315, all Y coordinates of each chemical profile obtained in step 307 are recalculated to be in correspondence with the Y coordinates of the Wimage. The warping matrix is used to retrieve the correspondence between the starting and ending coordinates of each line scan in the Image and in the Wimage, respectively. After this recalculation chemical profiles are automatically aligned to each other along the Y axis, and thus they can be summed up to improve the signal-to-noise ratio.

Figure 2E:
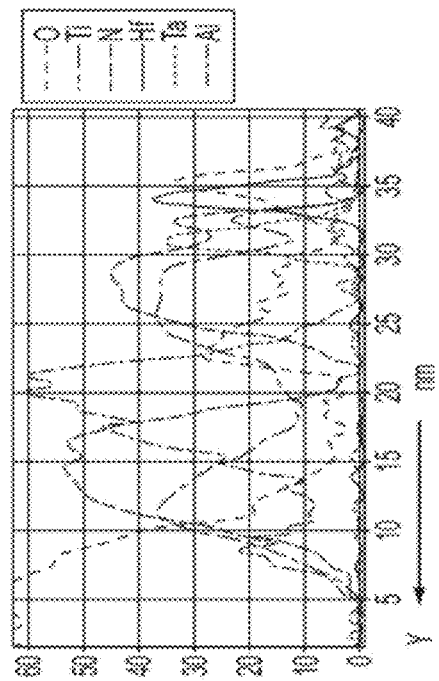
FIG. 2E illustrates the averaged chemical profiles obtained in accordance with an exemplary embodiment.
Figure 2G:
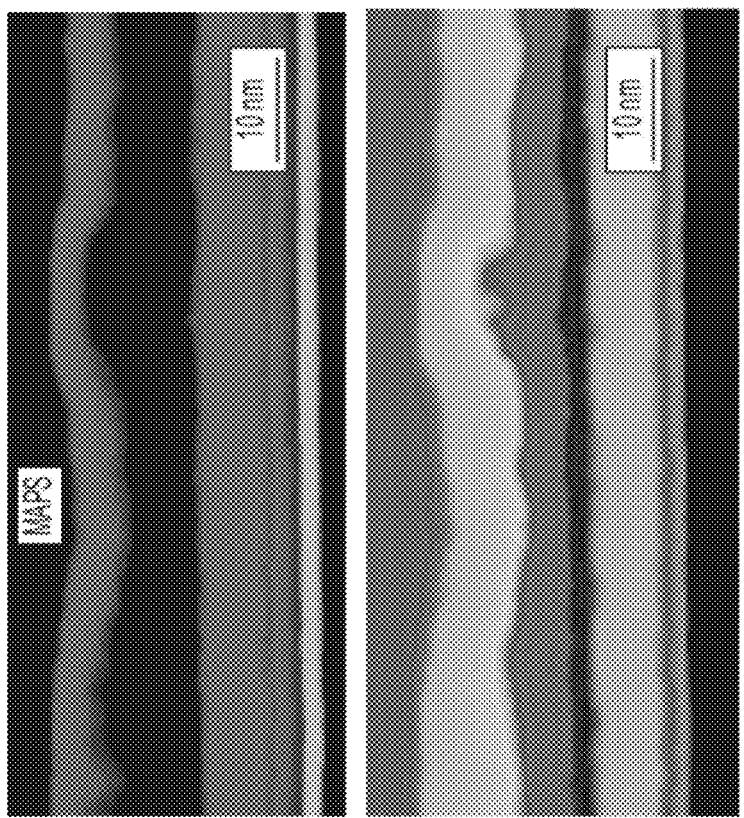
FIG. 2G illustrates Maps obtained, in accordance with an exemplary embodiment.

The aligned chemical profiles from several line scans are then averaged in step 317 forming an averaged chemical profile shown in FIG. 2E. Note that the averaged chemical profile shows much better signal-to-noise ratio as compared to the individual chemical profiles shown in FIG. 2C. Finally, the chemical profiles are expanded in the X direction to form a kind of chemical maps with no chemical variation along the X axis, hereinafter called Wmaps. As more than one element usually should be analyzed, the Wmaps can be conveniently displayed in the form of one or more RGB images in which each color strength corresponds to the content of a certain element as in FIG. 2F. The Wmaps do not contain extra information as compared with the averaged chemical profile in FIG. 2E. However, the two-dimensional format gives an advantage for further processing.

In developing the two-dimensional chemical maps, the directions and positions of the scanning lines generally have no impact, since the chemical information from all line scans is averaged in one direction and then transferred into a deformed image (e.g., FIG. 2D). However, in some situations, the number, directions, and positions of the scanning lines need to be considered in conjunction with the target of investigation. For example, if the target is a defect within a nanostructure, the number of scanning lines and the directions of the scanning lines may be determined based on known facts of the nanostructures as manufactured and known characteristics of the defect. If the nanostructure is a high power semiconductor laser diode with known chemical characteristics, the number of scanning lines and the directions of the scanning lines may be determined based on the possible position and dimensions of a target defect within the laser diode.

According to step 319, a reverse transformation of the Wmaps of FIG. 2F may be performed using a reverse transformation formula, e.g., an inversion of the warping matrix. Then, the two-dimensional chemical maps illustrated in FIG. 2G may be generated.

In accordance with another exemplary embodiment, the extraction of the chemical profiles may be omitted in step 307 and postponed until step 317. In that case, the raw spectra instead of chemical profiles may be aligned to the Y coordinates of the Wimage in step 315. The spectra then may be summed-up and averaged in step 317, while the chemical profiles may be extracted from the averaged spectra afterward. Such strategy (first average spectra—then extract chemical profiles) gives an advantage over the previously described strategy (first extract chemical profiles—then average chemical profiles) in cases where the spectra are extremely noisy. The advantage is, however, achieved at the expense of a much larger size of the treated data, as each spectrum consists of roughly of 1000 more bits than the extracted numbers of chemical composition.

The above-discussed methods can be used by any companies or laboratories conducting the characterization of nanostructures with scanning electron microscopy, for instance, optimization of metal fill in replacement gates in a layered nanostructure. The embodiments of the present disclosure can achieve several technical effects, including quickly producing two-dimensional chemical maps using standard slow-spectroscopy instruments instead of expensive fast-spectroscopy instruments. Further, the embodiments of the present disclosure provide two-dimensional chemical maps with high signal-to-noise ratios and minimize sample damage and improve the imaging resolution by applying a low electron dose to the examined area. The present disclosure enjoys industrial applicability in any of various types of highly integrated semiconductor technologies, particularly in 32 nm technology and beyond.

In the preceding description, the present disclosure is described with reference to specifically exemplary embodiments thereof. It will, however, be evident that various modifications and changes may be made thereto without departing from the broader spirit and scope of the present disclosure, as set forth in the claims. The specification and drawings are, accordingly, to be regarded as illustrative and not as restrictive. It is understood that the present disclosure is capable of using various other combinations and embodiments and is capable of any changes or modifications within the scope of the inventive concept as expressed herein.

What is claimed is:

1. A method comprising:
    fast two-dimensional scanning a layered nanostructure with a scanning electron microscope to form a structure image having multiple layers;
    slow-rate scanning the nanostructure along selected lines, collecting characteristic spectra;
    extracting chemical profiles of the nanostructure from the spectra;
    transforming the structure image into a warped structure image by flattening each of the layers in the structure image;
    aligning the coordinates of the chemical profiles to those of the warped structure image;
    averaging the chemical profiles obtained from different line scans;
    expanding the averaged profiles into warped chemical maps; and
    inversely transforming the warped chemical maps respectively into two-dimensional chemical maps.

2. The method according to claim 1, comprising slow-rate scanning the nanostructure along a few selected scanning lines.

3. The method according to claim 2, wherein each chemical profile includes one or more chemical elements.

4. The method according to claim 3, comprising transforming the structure image into a warped structure image by defining the morphology of the layers in the structure image by a criteria of equal signal levels, wherein the warped structure image shows no structural change along an axis within the plane of each of the layers.

5. The method according to claim 4, comprising:
transforming the structure image into the warped structure image using a transformation formula; and
inversely transforming the deformed chemical maps into the two-dimensional chemical maps using a reverse transformation formula corresponding to the transformation formula.

6. The method according to claim 5, wherein the transformation formula is a warping matrix that continuously transforms the structure image while preserving a topology of the structure image.

7. The method according to claim 6, wherein the warping matrix transforms the structural image by warping in one or two spatial directions.

8. The method according to claim 6, comprising transforming the chemical profiles into one averaged chemical profile by:
aligning the chemical profiles to the coordinates of the warped image; and
summing and averaging the chemical profiles.

9. The method according claim 8, wherein expanding the averaged chemical profiles forms warped chemical maps having no chemical change along one axis within the plane of each layer.

10. The method according to claim 1, comprising slow-rate scanning the nanostructure along selected scanning lines with employing electron energy loss spectroscopy, energy-dispersive X-ray spectroscopy, or cathode luminescence spectroscopy.

11. The method according to claim 1, comprising minimizing the electron dose required for the chemical characterization of a nanostructure.

12. A method comprising:
fast two-dimensional scanning a layered nanostructure with an electron probe, with registering an ADF or BF detector signal to provide an image of the nanostructure, the image having multiple layers;
generating a warped image by aligning the layers in the image using a warping matrix;
collecting spectra of the nanostructure along selected scan lines;
extracting chemical profiles from the collected spectra;
aligning and averaging the chemical profiles;
generating warped chemical maps from the averaged chemical profiles, the warped chemical maps having no chemical change along one axis within the plane of each layer; and
applying an inverse of the warping matrix to the warped chemical maps to form two-dimensional chemical maps of the nanostructure.

13. The method according to claim 12, comprising extracting chemical profiles from the spectra collected when scanning along a few selected lines.

14. The method according to claim 13, wherein each chemical profile includes multiple chemical elements.

15. The method according to claim 14, comprising:
generating warped chemical maps by: aligning and averaging the profiles for each chemical element; and
expanding the averaged chemical profiles to generate warped chemical maps having no chemical change along one axis within the plane of each layer.

16. The method according to claim 15, wherein the warping matrix continuously transforms the image of the nanostructure while preserving a topology of the image.

17. The method according to claim 16, wherein the warping matrix transforms the structural image by warping in one or two spatial directions.

18. The method according to claim 12, comprising extracting chemical profiles from the electron probe scanned along the predetermined lines while employing electron energy loss spectroscopy, energy-dispersive X-ray spectroscopy, or cathode luminescence spectroscopy.

19. A method comprising:
fast two-dimensional scanning a layered semiconductor nanostructure with an electron probe to form an image having multiple layers;
slow-rate scanning the nanostructure along a predetermined number of scan lines to form chemical profiles, each chemical profile corresponding to one of the scan lines and including multiple chemical elements;
transforming the image into a warped image by:
defining a morphology of the layers in the image with a criteria of equal signal levels; and
forming a warped image using a warping matrix that continuously transforms the image while preserving a topology of the image, wherein the warped image shows no structural change along each of the layers;
averaging chemical profiles from different line scans;
expanding an averaged chemical profile into the warped chemical maps;
aligning coordinates of the chemical profiles with those of the warped image;
averaging chemical profiles from different line scans for each chemical element;
expanding an averaged chemical profile into warped chemical maps, wherein each of the warped chemical maps exhibits no chemical change along an axis within the plane of each layer; and
inversely transforming the warped chemical maps into two-dimensional chemical maps using a reverse warping matrix corresponding to the warping matrix.

20. The method according to claim 19, comprising fast two-dimensional scanning the semiconductor nanostructure with registering the signal from an ADF or BF detector to form an image of the nanostructure.

* * * * *